United States Patent [19]

Ono et al.

[11] Patent Number: 4,569,948

[45] Date of Patent: Feb. 11, 1986

[54] PREPARATION PROCESS OF ACETIC ACID

[75] Inventors: Hiroshi Ono, Fujisawa; Masao Hashimoto, Yokohama; Eiiti Sugiyama, Odawara; Kenji Fujiwara, Yokohama; Kenji Yoshida, Fujisawa, all of Japan

[73] Assignees: Agency of Industrial Science and Technology; Extra-Ministerial Bureau of Ministry of International Trade and Industry, both of Japan

[21] Appl. No.: 633,507

[22] Filed: Jul. 23, 1984

Related U.S. Application Data

[63] Continuation of Ser. No. 433,783, Oct. 12, 1982, abandoned.

[30] Foreign Application Priority Data

Oct. 15, 1981 [JP] Japan .................................. 56-16344
Apr. 2, 1982 [JP] Japan .................................. 57-53766
Apr. 16, 1982 [JP] Japan .................................. 57-62344

[51] Int. Cl.⁴ ............................................ C07C 51/10
[52] U.S. Cl. .................................................... 518/700
[58] Field of Search ......................................... 518/700

[56] References Cited

U.S. PATENT DOCUMENTS 3,855,307 12/1974 Rony et al. .
4,332,915 6/1982 Knifton et al. .
4,362,821 12/1982 Lin .
4,366,259 12/1982 Knifton et al. .

FOREIGN PATENT DOCUMENTS 0033425 8/1981 European Pat. Off. ............ 518/700

OTHER PUBLICATIONS

Chemical Abstracts, 95:219767a.

*Primary Examiner*—Howard T. Mars
*Attorney, Agent, or Firm*—Fisher, Christen & Sabol

[57] ABSTRACT

This invention relates to a process for preparing acetic acid from carbon monoxide gas and hydrogen gas, which process comprises catalytically reacting carbon monoxide gas and hydrogen gas under elevated pressures and in a liquid medium containing a ruthenium compound, cobalt compound and promoter(s).

9 Claims, No Drawings

PREPARATION PROCESS OF ACETIC ACID

This is a continuation application of Ser. No. 433,783, filed on Oct. 12, 1982, abandoned.

BACKGROUND OF THE INVENTION

1. Field of the Invention

This invention relates to a process for preparing acetic acid using carbon monoxide gas and hydrogen gas as raw materials. Carbon monoxide gas and hydrogen gas are catalytically reacted under elevated pressures in a liquid medium containing a ruthenium compound, cobalt compound and promoter(s).

2. Description of the Prior Art

There have been known several examples of the so-called direct process which uses carbon monoxide gas and hydrogen gas as raw materials to directly synthesize acetic acid. For example, U.S. Pat. No. 4,235,801 and U.S. Pat. No. 4,246,186 disclose a process for obtaining a hydrocarbon and an oxygen-containing compound by reacting carbon monoxide and hydrogen gas in the presence of rhodium carried on a carrier such as silica gel in accordance with the gas-phase heterogeneous process. According to the above process, the selectivity of carbon monoxide consumed during the reaction into acetic acid (hereinafter called "acetic acid selectivity") was however limited to low values of 30% and so. Furthermore, the above process is accompanied by such a drawback that hydrocarbons such as methane and the like occur as by-products in large volumes and their separation from the gaseous mixture of unreacted carbon monoxide and hydrogen gases is extremely difficult. On the other hand, U.S. patent application Ser. No. 590,717 filed June 26, 1975 and U.S. Pat. No. 4,014,913 disclose a similar gas-phase heterogeneous process which makes use of a rhodium-manganese catalyst instead of the above-described rhodium. However, the acetic acid selectivity of this process is still around 30% or so. It is difficult to say that the by-production problem of hydrocarbons has been improved. Furthermore, U.S. Pat. Nos. 4,224,236 and 4,288,558 (DE-OS No. 2,814,427 and DE-OS No. 2,814,365) describe another gas-phase heterogeneous process in which the reaction is carried out in the presence of a catalytic system of rhodium added with magnesium and a base. According to this process, the acetic acid selectivity has been improved to a substantial extent. However, it still produces the by-product, methane, as much as several percents to forty percents.

There is thus a strong demand for the development of a preparation process of acetic acid, which process has improved the drawbacks of such prior art processes as referred to in the above.

SUMMARY OF THE INVENTION

An object of this invention is to provide an improved preparation process of acetic acid using carbon monoxide gas and hydrogen gas as raw materials.

Another object of this invention is to provide a novel catalytic system which enables to obtain acetic acid and acetates with high degrees of selectivity in the above process.

A further object of this invention is to provide a preparation process of acetic acid, which process does not produce too much hydrocarbon byproducts such as methane that are difficult to remove upon recycling and reutilizing unreacted carbon monoxide.

A still further object of this invention is to provide a liquid phase process which permits easy removal of a great deal of heat to be generated as the reaction proceeds.

These objects have been achieved by the finding of the present inventors that acetic acid and an acetate such as methyl acetate or ethyl acetate can be obtained with high degrees of selectivity by using a ruthenium compound and cobalt compound as catalysts and further adding a certain promoter and use of such catalysts and promoter results in extremely little occurrence of undesirous hydrocarbon by-products such as methane.

It is preferable to use, as such a promoter, (a) at least one basic compound containing at least one element in Group Va of the periodic table and/or (b) at least one halide. The basic compound may preferably be at least one compound selected from the group consisting of amines, phosphines, arsines, stibines and bismuthines. On the other hand, the halide is preferably at least one compound selected from the group consisting of alkali metal halides, alkaline earth metal halides, quaternary ammonium halides, phosphonium halides and iminium halides.

It is particularly preferable to use, as the basic compound, a phosphorus compound represented by the general formula (I) and/or another phosphorus compound represented by the general formula (II):

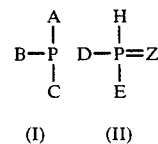

in which A, B, C, D and E are the same or different and mean individually a hydrogen or halogen atom, an alkyl group having 1-20 carbon atoms, substituted alkyl group, aryl group, substituted aryl group or acyl group, or an —OR′, —SR″ or —N(R‴)₂ group —R, R″ and R‴ being individually a hydrogen atom, an alkyl or aryl group which has 1-20 carbon atoms and may optionally be substituted, or an acyl group—, two or more of A, B and C or D and E may be coupled together to form a ring, and Z denotes an oxygen or sulfur atom.

As the halide, it is suitable to employ one or more iminium halides or a mixture of at least one iminium halide and at least one phosphonium halide.

According to the process of this invention, acetic acid can be prepared with excellent selectivity. Furthermore, it is possible to convert with ease an acetate such as methyl acetate or ethyl acetate, which is obtained by the practice of the process of this invention, into acetic acid by simple hydrolysis. Such acetates are on the other hand useful as industrial reagents or solvents as they are. Accordingly, they may be separated as acetates from the reaction mixture.

In the process of this invention, the term "acetic acid" will hereinafter mean not only acetic acid per se but also the acetic acid moieties contained in such acetates as mentioned above.

DETAILED DESCRIPTION OF THE INVENTION

The ruthenium compound useful in the practice of the process of this invention is a ruthenium compound capable of forming a complex together with carbon monoxide as a ligand. Under the reaction conditions, it is present as a ruthenium complex having carbon monoxide ligands and is dissolved in a liquid medium used. This ruthenium complex can be formed under the reaction conditions, using one of various ruthenium compounds as its precursor. Any ruthenium compounds may be used as such precursors so long as they can form ruthenium complexes having carbon monoxide ligands under the reaction conditions. As exemplary ruthenium compounds, may be mentioned, besides metallic ruthenium, ruthenium oxides such as ruthenium dioxide and ruthenium tetraoxide, their hydrates, ruthenium chloride, ruthenium iodide, ruthenium salts of mineral acids such as ruthenium nitrate, and ruthenium salts of organic acids such as ruthenium acetate and ruthenium propionate. In addition, ruthenium compounds in the forms of coordination compounds may be used as they are. Illustrative of such ruthenium compounds include ruthenium carbonyls such as triruthenium dodecacarbonyl, ruthenium complexes obtained by coordinating ruthenium with a variety of ligands including oxygen, sulfur, halogen, nitrogen, phosphorus, arsenic, antimony and bismuth atoms, and their salts.

Among the above-described ruthenium compounds, it is preferred to use a ruthenium oxide, ruthenium halide, ruthenium carbonyl or a ruthenium complex in which at least part of its carbon monoxide ligands is replaced by another or other ligands.

By the term "cobalt compound" as used herein, is also meant a cobalt compound which is capable of forming a cobalt complex containing carbon monoxide moieties as its ligands under the reaction conditions and is dissolved in a liquid medium to be employed. Similar to the ruthenium compound, such complexes may be prepared under the reaction conditions using a variety of cobalt compounds as precursors. Accordingly, any cobalt compounds may be used as such precursors so long as they can afford under the reaction conditions cobalt complexes having carbon monoxide ligands. As examples of such cobalt complexes, may be mentioned, besides metallic cobalt, cobalt oxides, cobalt hydroxides, cobalt chloride, cobalt iodide, cobalt salts of mineral acids such as cobalt nitrate, and cobalt salts of organic acids such as cobalt acetate, cobalt benzoate and cobalt naphthenate. Besides, it is also feasible to employ coordination compounds. As exemplary coordination compounds, may be mentioned cobalt carbonyls such as dicobalt octacarbonyl, tetracobalt dodecacarbonyl and cyclopentadienyl cobalt dicarbonyl, cobalt complexes obtained by coordinating with ligands containing, for example, oxygen, sulfur, halogen, nitrogen, phosphorus, arsenic, antimony and/or bismuth atoms, and their salts. Among such cobalt compounds, it is preferred to use a cobalt oxide, cobalt halide, cobalt carbonyl, cobalt salt of an organic acid, or a cobalt complex in which at least part of carbon monoxide ligands of a cobalt carbonyl is replaced by another or other ligands. It is also possible to use, besides those described above, a compound containing both ruthenium and cobalt as a precursor for the ruthenium or cobalt compound. As examples of such compounds, may be mentioned heteronuclear clusters of ruthenium and cobalt such as those represented by the formula: $M[RuCo_3(CO)_{12}]$ or $M[CoRu_3(CO)_{13}]$ in which M stands for a hydrogen atom or a cation.

In the process of this invention, the ruthenium compound and cobalt compound are each considered to be present in a dissolved state in the liquid medium under the reaction conditions, as a complex coordinated with at least one molecule of carbon monoxide ligand per its one atom and, in some instances, other ligand or ligands such as Lewis base added as a promoter. Although it is not clear whether the thus-dissolved ruthenium compound and cobalt compound form under the reaction conditions a heteronuclear cluster, for example, the aforementioned complex such as $M[CoRu_3(CO)_{13}]$, the effects of this invention have first been brought about by the presence of both of the ruthenium and cobalt compounds.

It is indispensable to use a promoter in the process of this invention. By the term "promoter" as used herein, is meant an additive which accelerates the synthesis of acetic acid by the thus-dissolved ruthenium compound and cobalt compound, both jointly serving as a main catalyst, and serves to improve the selectivity of carbon monoxide into acetic acid.

As such a promoter, may be employed (a) at least one basic compound containing at least one element in Group Va of the periodic table, such as nitrogen, phosphorus, arsenic, antimony, bismuth or the like, and/or (b) at least one halide. Particularly good results can be obtained when a basic compound (a) and a halide (b) are used in combination. Incidentally, the term "basic compound" as used herein means a compound having the nature of the Lewis bases and is a generic term for compounds having a non-covalent electron pair.

As basic compounds (a) containing at least one element in Group Va of the periodic table, may for example be mentioned amino compounds, imino compounds, nitrilo compounds, amides and cryptandes. Exemplary basic compounds (a) include preferably tributyl amine, triphenyl amine, pyridine, 2-hydroxypyridine and the like. On the other hand, as a phosphorus-containing compound, may be mentioned a phosphorus compound represented by the general formula (I) or (II):

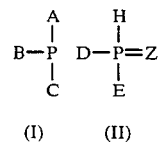

(I)    (II)

in which A, B, C, D and E are the same or different and mean individually a hydrogen or halogen atom, an alkyl group having 1-20 carbon atoms, substituted alkyl group, aryl group, substituted aryl group or acyl group, or an —OR', —SR" or —N(R''')₂ group —R, R" and R''' being individually a hydrogen atom, an alkyl or aryl group which has 1-20 carbon atoms and may optionally be substituted, or an acyl group—two or more of A, B and C or D and E may be coupled together to form a ring, and Z denotes an oxygen or sulfur atom.

The phosphorus compounds represented by the above general formula (I) or (II) may be, more specifically speaking by way of illustration, phosphorus compounds represented by the following general formula (1), (2), (3) or (4):

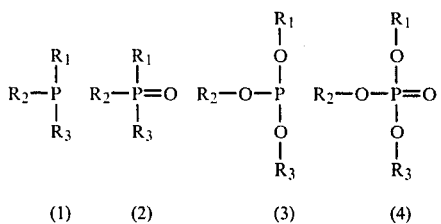

(1) (2) (3) (4)

in which $R_1$, $R_2$ and $R_3$ are the same or different and mean individually a hydrogen or halogen atom or an alkyl group having 1-20 carbon atoms, aryl group, alkyloxy group or cycloalkyl group.

The phosphorus compound of the general formula (II) useful in the practice of the process of this invention may be considered, where at least one of A, B and C stands for —OR' group in the general formula (I), as an isomer of its corresponding phosphorus compound which is represented by the general formula (I) and is readily formed at the equilibrium of the following equation:

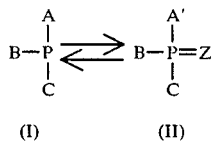

(I)    (II)

in which Z is an oxygen or sulfur atom and A' stands for a hydrogen atom.

The phosphorus compound represented by the above general formula (I) or (II) can bring about unexpectedly better results as a promoter, compared with other basic compounds which may also be used as promoters. In other words, the characteristic effects of the phosphorus compound as a promoter are, inter alia, that (1) it improves the activity of a catalyst to a considerable extent; (2) it considerably increases the molar ratio of (resulting ethanol+resulting acetic acid) to (resulting methanol); and (3) it improves the selectivity into acetic acid as it can control the molar ratio of resulting ethanol to resulting acetic acid.

As exemplary phosphorus compounds useful in the practice of the process of this invention, may be mentioned as follows:

(1) Phosphines such as trimethyl phosphine, triethyl phosphine, tripropyl phosphine, tributyl phosphine, triphenyl phosphine, etc.;

(2) Phosphorus salts of oxy acid and phosphorus halides:

Phosphorous acid, phosphonic acid, phosphonous acid, phosphinic acid (hypophosphorous acid), phosphinous acid, phosphine oxide , and other oxy acids containing a phosphorus atom having an oxidation number of 3 or smaller.

Phosphorus halides such as $PF_3$, $PCl_3$, $PBr_3$, $PI_3$, $PBr_2Cl$ and $PBrCl_2$;

(3) Oxy acids of organophosphorus compounds and their esters:

Oxy acid esters having high molecular weights, for example, the phosphorous acid ester of polyvinyl alcohol, may be used. However, satisfactory results can generally be obtained when an oxy acid containing an organic group having 1-20 carbon atoms or its ester is employed. As such oxy acids and oxy acid esters, may for example be mentioned phosphorous triesters and their condensation compounds such as trimethyl phosphite, triethyl phosphite, tridecyl phosphite, triphenyl phosphite, tri-p-chlorophenyl phosphite, dimethylethyl phosphite, 1,2-[(C_2H_5O)_2PO]_2C_6H_5, [(C_6H_5O)_2POCH_2]_3N,

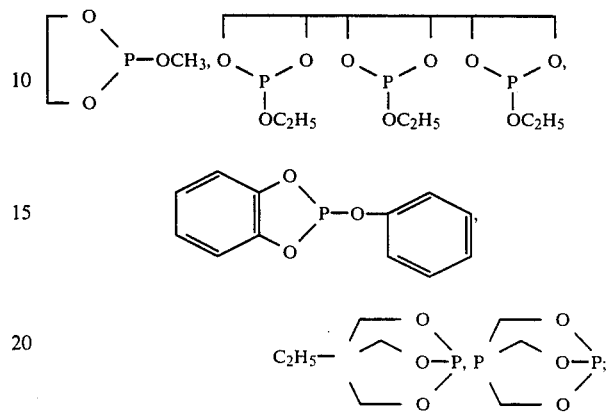

phosphorous diesters such as dimethyl phosphite, diphenyl phosphite, dibenzyl phosphite, ethylphenyl phosphite, ethylene phosphite and the like; phosphorous monoesters such as, for example, 2-chloroethyl phosphite, phenyl phosphite, methyl phosphite, etc.; acyl phosphites such as, for example, triacetyl phosphite, monoacetyl phosphite, butyldiacetyl phosphite, and

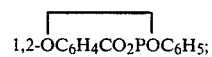

1,2-$OC_6H_4CO_2POC_6H_5$;

phosphonic esters and their condensation compounds such as, for example, diphenyl phosphonate, [(CH_3O)P(O)(H)O]_2(CH_2)_2 and (C_2H_5O)P(O)(H)OP(O)(OC_2H_5)_2. Besides, may also be employed oxy acids of organophosphorus compounds such as phenyl phosphinic acid, ethyl phosphinic acid, benzyl phosphinic acid, diphenyl phosphinous acid, diethyl phosphinous acid, dicyclohexyl phophinous acid, phenyl phosphinic acid, and t-butyl phosfinic acid; and esters of oxy acid such as dimethylphenyl phosphonite, methylbutylphenyl phosphonite, phenylethyl phosphonite, n-butyldiphenyl phosphonite, methyldiethyl phosphonite, diacetylphenyl phosphonite and $(CH_3O)(O)P(H)(C_6H_5)$;

(4) Halides of oxy acids:

For example, methyl phosphorate difluoride, ethyl phosphorate dichloride, phenyl phosphorate dibromide, diphenyl phosphorate chloride, ethylene chlorophosphite, phenylphosphonous chloride, methyl phenylphosphonous bromide, diphenylphosphinous chloride, and diethylphosphinous bromide;

(5) The same compounds as those given as examples in the above categories (1)-(3) except that a part of or all the oxygen atoms have been substituted by sulfur atoms, for example, trimethyl thiophosphite, tribenzyl thiophosphite, $(C_2H_5S)_2(C_6H_5O)P$, $[(C_2H_5O)_2P]_2S$, $[(C_2H_5)NC(S)S-]_3P$, $(CH_3O)_2PSH$, $CH_3SPCl_2$, $(C_6H_5S)_2PCl$ and phenyl thiophosphonous acid; and (6) Similarly, compounds containing an N—P bond, for example, amide compounds such as $[(CH_3)_2N]_3P$, $[(CH_3)_2N]_2POC_2H_5$, $[(CH_3)_2N]_2POH$, $(C_6H_5NH)_2POH$, $(CH_3O)_2PN(CH_3)_2$ and $(C_2H_5)_2NPCl_2$.

Among the above-described phosphorus compounds, those described in the above catagories (1)–(4) are preferred. Furthermore, it is of course possible to effectively use compounds which are readily converted into compounds of the general formula (I) or (II) under the reaction conditions of the process of this invention, e.g., the same compounds as those represented by the general formula (I) or (II) except that their phosphorus atoms have each been replaced by a =P—O—(P) bond, ≡P—O—(P) bond, =Si—O—(P) bond, =Sn—O—(P) bond, =Ge—O—(P) bond or the like and phosphorus salts of oxy acids.

As examples of arsenic-containing compounds, antimony-containing compounds and bismuth-containing compounds, may be mentioned the same compounds as those represented by the general formula (I) except that their phosphorus atoms have been replaced by arsenic, antimony or bismuth atoms. Stibines, arsines and bismuthines such as triphenyl stibine, triphenyl arsine and triphenyl bismuthine are preferred. Alternatively, it is possible to use compounds containing two or more elements in Group Vb such as diamines and diphosphines.

As halides (b) useful in the practice of the process of this invention, may be mentioned for example, inorganic halides such as alkali metal halides, alkaline earth metal halides and rare earth metal halides, including for example sodium iodide, potassium bromide, lithium chloride, barium iodide and the like; quaternary ammonium halides represented by the formula (III):

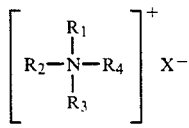

in which $R_1$, $R_2$, $R_3$ and $R_4$ are individually an alkyl, aryl, alkyloxy or cycloalkyl group and $X^-$ means a halogenic anion such as $Cl^-$, $Br^-$ or $I^-$; and phosphonium salts similar to the compounds represented by the general formula (III) except that their nitrogen atoms have been replaced by phosphorus atoms. Besides, quaternary ammonium salts including cyclic amines and halides having such a form as an iminium salt are effective to achieve the objects of this invention.

These iminium salts and phosphonium salts are respectively represented by the following general formulae (IV) and (V):

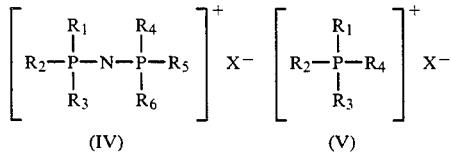

in which $R_1$, $R_2$, $R_3$, $R_4$, $R_5$ and $R_6$ mean individually an alkyl, aryl, alkyloxy or cycloalkyl group having 1–20 carbon atoms, and $X^-$ denotes an anion.

As more specific iminium salts, may be mentioned for example, mineral acid salts and organic acid salts of bis(triorganophosphine)iminium such as bis(triphenylphosphine) iminium chloride, bis(triphenylphosphine)iminium bromide and bis(triphenylphosphine)iminium iodide.

On the other hand, exemplary phosphonium salts include mineral acid salts and organic acid salts of phosphonium such as tetramethylphosphonium chloride, tetra-n-butylphosphonium iodide, tetraphenylphosphonium bromide, methyltriphenylphosphonium bromide, ethyltriphenylphosphonium bromide, n-butyltriphenylphosphonium bromide, n-hexyltriphenylphosphonium bromide, n-heptyltriphenylphosphonium bromide, and benzyltriphenylphosphonium bromide.

A mixture of an iminium salt represented by the above formula (IV) and a phosphonium salt represented by the above formula (V) may be used as a preferable promoter.

In the process of the present invention, the above described wide variety of promoters may be used singly or as a mixture of two or more of the promoters. Particularly preferred combinations are (i) the combination of a halide and one or more phosphorus compound represented by the general formulae (I) and/or (II); and (ii) the combination of a phosphorus compound represented by the general formula (I) and/or another phosphorus compound represented by the general formula (II), an iminium salt represented by the general formula (IV) and a phosphonium salt represented by the general formula (V).

Any liquid media may be employed in the practice of the process of this invention so long as they are present at least in part as liquid under the reaction conditions. As examples of such liquid media, may be mentioned saturated hydrocarbons, aromatic hydrocarbons, halogenated hydrocarbons, ethers, esters, alcohols, carboxylic acids, carboxylic anhydrides, amides, substituted and unsubstituted amines, sulfones, water and silicone. These liquid media may be either inert to the reaction such as saturated hydrocarbons or reactive to the reaction such as alcohols, which form esters with resulting acetic acid. Furthermore, it is still possible to use those having effects as promoters, for example, amines.

Among such liquid media, aprotic liquid media are more preferably used in the process of this invention. Exemplary aprotic liquid media include saturated hydrocarbons and aromatic hydrocarbons such as, for example, heptane, octane, cyclohexane, decalin, tetralin, kerosine, benzene, toluene and xylene; halogenated hydrocarbons such as, for instance, chloropentane, o-dichlorobenzene, o-chlorotoluene and fluorobenzene; ethers such as, for example, dioxane, tetrahydrofuran, diethyl ether, diglyme, tetraglyme, 15-crown-5 and 18-crown-6; esters such as, for example, methyl acetate, ethyl butyrate and γ-butylolactone; ketones such as, for example, acetone, methyl ethyl ketone and acetophenone; amides such as, for example, N,N-dimethylformamide; lactams and their derivatives such as, for example, 2-pyrrolidone, ε-caprolactam and N-methylpyrrolidone; amines such as ethylamine, ethylene diamine, cyclohexylamine, N-methylaniline, N,N-diethylaniline, morpholine, N-methylmorpholine, pyridine, picoline, 2-hydroxypyridine and quinoline; sulfones such as, for example, sulfolan; and sulfoxides such as, for instance, dimethylsulfoxide.

When using an iminium salt and/or phosphonium salt as promoters, it is particularly preferred to employ an aprotic low polar liquid medium as the liquid medium. Such an aprotic low polar liquid medium is preferably an aprotic low polar solvent having a dielectric constant (ε) not greater than 20 as defined in J. A. Riddick et al, Organic Solvents, 2nd Ed., (1955). Use of hydrocarbons or halogenated hydrocarbons is particularly preferred. For example, saturated hydrocarbons such as pentane, hexane, heptane, cyclohexane and decalin as well as aromatic hydrocarbons such as benzene, toluene, xylene, tetralin and kerosine are preferred. Alternatively, it is possible to use as preferable liquid media chlorobenzene, bromobenzene, o-dichlorobenzene and o-chlorotoluene. In addition, it is also possible to use low polar oxygen-containing compounds such as tetrahydrofuran, dioxane, anisole and diphenyl ether.

These liquid media may be used solely or as a mixture of two or more of the liquid media.

In the process of this invention, there is no particular limitation vested on the reaction temperature. However, the lower limit may be determined at such a temperature as to obtain a practical reaction velocity. On the other hand, the upper limit may also be determined under such conditions that the partial pressure of carbon monoxide required to make the ruthenium and cobalt compounds soluble will not become extremely high, the decomposition and reaction of the promoter will be suppressed, the mechanical strength of materials making up the preparation apparatus will not be considerably lowered, the corrosion of the materials will not be substantially promoted, and undesirous side reactions yielding methane and the like will be retarded. The reaction temperature range is generally 150°–300° C., and preferably 170°–280° C.

In the process of this invention, the lower limit of the reaction pressure is subjected to a limitation in view of the minimum carbon monoxide partial pressure required to dissolve at the reaction temperature the ruthenium and cobalt compounds which serve as the main catalyst and the minimum hydrogen gas partial pressure required to maintain a practical reaction velocity. Its upper limit is also subjected to a limitation from the economical consideration such as the withstandable upper pressure level of the reaction apparatus and power required to compress carbon monoxide gas and hydrogen gas as raw materials.

Generally speaking, the reaction pressure range is 80–3000 kg/cm$^2$G, preferably 150–1000 kg/cm$^2$G, and more preferably 300–700 kg/cm$^2$G.

The molar ratio of carbon monoxide gas to hydrogen gas, both used as raw materials for the synthesis, is 1:1 stoichiometrically. The reaction can however proceed satisfactorily at molar ratios other than the above one. As parameters limiting the range of the molar ratio, there are for example the reaction velocity and acetic acid selectivity. In view of these parameters, the molar ratio range of 1:10–10:1 is generally employed. However, as an extreme example, the process of the present invention may be carried out even if pure carbon monoxide gas is used in the presence of water or pure hydrogen gas is employed in the presence of carbon dioxide, provided that suitable reaction conditions will be chosen. No problem or inconvenience will arise even if the gaseous mixture of the raw materials contains other components inert to the reaction, for example methane and nitrogen gases.

The ruthenium compound and cobalt compound to be used in the process of this invention may generally be present in the liquid medium at a concentration level within 0.1–100 parts by weight as the total weight of pure ruthenium and cobalt based on 1000 parts by weight of the liquid medium. On the other hand, the ruthenium compound and cobalt compound may be used in an atomic ratio of 300:1–1:10 as calculated in terms of ruthenium and cobalt.

The amount of the promoter to be used in the process of this invention is governed by its relative amount to the amounts of both ruthenium compound and cobalt compound to be used as catalysts. The promoter cannot exhibit noticeable effects when used too little. On the contrary, its effects may be adversely affected if used too much. The preferable range of the promoter to be added is as follows based on the sum of the gram atom number of ruthenium in the ruthenium compound and the gram atom number of cobalt in the cobalt compound. Namely, with respect to a basic compound containing at least one element in Group Va, it may be used in a mole number 0.001–10 times, and preferably 0.01–2 times the sum of the gram atom numbers of the above-defined ruthenium and cobalt. On the other hand, regarding a halide, the promoter may be used in a mole number 0.001–100 times, and preferably 1–60 times the sum of the gram atom numbers of the same ruthenium and cobalt.

The process of this invention may be practiced by each of the batch method, semi-continous method and continuous method.

The ruthenium and cobalt compounds, promoter and liquid medium may be added at the beginning to a reactor by the batch method. Alternatively, they may also be added by the semi-continuous or continous method.

The reaction product may be collected in a manner commonly known in the art, for example, by the distillation or stripping method. In some instances, a resulting acetate may be hydrolyzed into acetic acid and its corresponding alcohol, which may thereafter be collected separately. The catalyst, promoter and liquid medium may be recycled to the reactor for their reutilization.

The process of the present invention has, inter alia, the following merits compared with conventional direct synthesis process of acetic acid:

(1) It enjoys high selectivity of acetic acid including the acetic acid moiety of each acetate which moiety can be readily converted into acetic acid by hydrolysis;

(2) It produces extremely little hydrocarbonaceous by-products such as methane, which by-products are difficult to remove upon recycling and reutilizing unreacted carbon monoxide gas and hydrogen gas; and (3) It permits easy removal of a great deal of heat to be generated as the reaction proceeds, because the reaction is carried out in a liquid phase.

The process of this invention will hereinafter be described in further detail by the following examples.

EXAMPLE 1

A stainless steel made autoclave having the internal capacity of 50 ml was charged with 0.15 g of triruthenium dodecacarbonyl [Ru$_3$(CO)$_{12}$], 0.12 g of dicobalt octacarbonyl [Co$_2$(CO)$_8$], 3.1 g of n-heptyltriphenylphosphonium bromide, 0.18 g of triphenyl phosphine and 19 ml of toluene, followed by charging a mixed gas of carbon monoxide gas and hydrogen gas (the molar ratio of CO to H$_2$=1:1) at room temperature to 280 kg/cm$^2$G. The autoclave was heated with stirring to 220° C., where it was held for 3 hours to carry out the reaction. During this period of time, the internal pressure of the autoclave changed to 375–365 kg/cm$^2$G. Then, the heating of the autoclave was stopped and the autoclave was cooled to room temperature. Thereafter, its internal pressure was released and its contents were taken out and analyzed by gas chromatograph.

The liquid reaction mixture consisted of two phases and contained, as the total amounts in both of the phases, 75.9 mg of acetic acid, 1.5 mg of methyl acetate, 15.5 mg of ethyl acetate, 0.8 mg of methanol, 6.8 mg of ethanol, 0.7 mg of n-propanol and a trace amount of methyl formate. A trace amount of methane was detected in the gas phase.

EXAMPLES 2–17

The procedure of Example 1 was repeated using different basic compounds, halides, liquid media, reaction temperatures, reaction pressures and molar ratios of carbon monoxide gas to hydrogen gas. Results are shown in Table 1, together with the results of Example 1.

In Table 1, the symbols will respectively indicate the following compounds:

Ru-A : Triruthenium dodecacarbonyl [$Ru_3(CO)_{12}$]
Co-A : Dicobalt octacarbonyl [$Co_2(CO)_8$]
TPP : Triphenyl phosphine ($Ph_3P$)
P : Pyridine ($C_5H_5N$)
TBr : n-Heptyltriphenyl phosphonium bromide (n-$HpPh_3PBr$)
BCl : Benzyltriphenyl phosphonium chloride ($BzPh_3PCl$)
NaI : Sodium iodide
G : Gamma-butylolactone
TPA : Triphenylarsine
TPB : Triphenylbismuthine
HTBr : n-Hexyltriphenyl phosphonium bromide
BTBr : n-butyltriphenyl phosphonium bromide
CPBr : Cetylpyridinium bromide
T : Toluene
S : Sulfolan
D : Benzene
o-X : Orthoxylene
o-Cl-B: Orthochlorobenzene

TABLE 1

| Ex. No. | Catalysts (Ru & Co compounds) (g) | | Promoter (g) | | Liquid medium (ml) | Reaction temp. (°C.) | Max. reaction pressure (kg/cm² G) | CO/$H_2$ molar ratio |
|---|---|---|---|---|---|---|---|---|
| 1 | Ru—A | 0.15 | TPP | 0.18 | T | 19 | 220 | 375 | 1 |
|   | Co—A | 0.12 | TBr | 3.1 | | | | | |
| 2 | Ru—A | 0.15 | TPP | 0.18 | S | 19 | 220 | 378 | 1 |
|   | Co—A | 0.12 | B-Cl | 2.72 | | | | | |
| 3 | Ru—A | 0.15 | TPP | 0.18 | T | 19 | 220 | 340 | 1 |
|   | Co—A | 0.12 | TBr | 1.24 | | | | | |
| 4 | Ru—A | 0.15 | TPP | 0.18 | T | 19 | 220 | 370 | 1 |
|   | Co—A | 0.04 | TBr | 3.1 | | | | | |
| 5 | Ru—A | 0.15 | TPP | 0.18 | B | 19 | 220 | 330 | 2 |
|   | Co—A | 0.12 | TBr | 3.1 | | | | | |
| 6 | Ru—A | 0.15 | TPP | 0.18 | O—X | 19 | 240 | 390 | 1 |
|   | Co—A | 0.12 | TBr | 3.1 | | | | | |
| 7 | Ru—A | 0.3 | TPP | 0.36 | O—Cl—B | 19 | 220 | 380 | 1 |
|   | Co—A | 0.24 | TBr | 6.2 | | | | | |
| 8 | Ru—A | 0.15 | TPP | 0.36 | T | 19 | 220 | 380 | 1 |
|   | Co—A | 0.24 | TBr | 3.1 | | | | | |
| 9 | Ru—A | 0.15 | TPP | 0.18 | T | 19 | 220 | 350 | 1 |
|   | Co—A | 0.01 | TBr | 3.1 | | | | | |
| 10 | Ru—A | 0.15 | TPP | 0.06 | T | 19 | 220 | 365 | 1 |
|   | Co—A | 0.04 | TBr | 3.1 | | | | | |
| 11 | Ru—A | 0.15 | TPP | 0.18 | T | 19 | 220 | 360 | 1 |
|   | Co—A | 0.12 | TBr | 6.2 | | | | | |
| 12 | Ru—A | 0.15 | TPP | 0.18 | S | 19 | 220 | 380 | 1 |
|   | Co—A | 0.12 | TBr | 3.1 | | | | | |
|   |   |   | NaI | 2.1 | | | | | |
| 13 | Ru—A | 0.15 | P | 0.277 | S | 19 | 220 | 360 | 1 |
|   | Co—A | 0.12 | TBr | 3.1 | | | | | |
| 14 | Ru—A | 0.15 | LiI | 0.94 | S | 19 | 220 | 364 | 1 |
|   | Co—A | 0.12 | | | | | | | |
| 15 | Ru—A | 0.15 | TPA | 0.071 | T | 19 | 220 | 365 | 1 |
|   | Co—A | 0.04 | HTBr | 3.0 | | | | | |
| 16 | Ru—A | 0.15 | TPB | 0.103 | G | 19 | 220 | 380 | 1 |
|   | Co—A | 0.04 | BTBr | 2.8 | | | | | |
| 17 | Ru—A | 0.15 | TPP | 0.06 | S | 19 | 220 | 365 | 1 |
|   | Co—A | 0.04 | CPBr | 2.69 | | | | | |

| Ex. No. | Reaction time (hrs.) | Reaction products (mg) | | | | | | |
|---|---|---|---|---|---|---|---|---|
| | | Acetic acid | Methyl acetate | Ethyl acetate | Methanol | Ethanol | Propanol | Methane |
| 1 | 3 | 75.9 | 1.5 | 15.5 | 0.8 | 6.8 | 0.7 | 0 |
| 2 | 3 | 27.5 | 0 | 35.8 | 89.7 | 18.2 | 0.1 | 0.1 |
| 3 | 3 | 21.0 | 35.0 | 8.1 | 23.2 | 19.4 | 1.3 | 0 |
| 4 | 3 | 238.9 | 67.2 | 73.7 | 9.0 | 30.5 | 3.22 | 8.7 |
| 5 | 3 | 99.4 | 18.8 | 14.8 | 1.5 | 5.5 | 0.6 | 0.2 |
| 6 | 3 | 216.1 | 8.7 | 57.1 | 1.4 | 16.1 | 5.6 | 2.8 |
| 7 | 3 | 131.4 | 12.0 | 32.0 | 2.8 | 31.7 | 8.3 | 2.4 |
| 8 | 3 | 49.0 | 4.4 | 7.8 | 1.4 | 9.8 | 2.1 | 0 |
| 9 | 3 | 116.0 | 112.1 | 40.5 | 12.3 | 73.4 | 4.2 | 21.1 |
| 10 | 3 | 242.5 | 150.1 | 84.2 | 29.7 | 64.1 | 6.6 | 16.5 |
| 11 | 3 | 203.0 | 159.7 | 27.4 | 3.4 | 9.8 | 0.5 | 0 |
| 12 | 3 | 15.0 | 5.4 | 0.1 | 48.5 | 21.4 | 0 | 0 |
| 13 | 3 | 80.2 | 142.4 | 43.8 | 205.9 | 100.9 | 12.1 | 7.1 |
| 14 | 3 | 0 | 6.7 | 1.7 | 101.1 | 36.1 | 3.3 | 0.1 |
| 15 | 3 | 194.9 | 20.8 | 141.2 | 48.8 | 79.9 | 10.5 | 22.1 |
| 16 | 3 | 69.0 | 66.7 | 15.8 | 154.0 | 36.4 | 2.8 | 0 |

TABLE 1-continued

| | | | | | | | |
|---|---|---|---|---|---|---|---|
| 17 | 3 | 14.2 | 23.3 | 1.4 | 143.4 | 25.7 | 1.1 | 0 |

EXAMPLE 18

The procedure of Example 1 was repeated except that, in place of 0.15 g of triruthenium dodecacarbonyl, ruthenium oxide ($RuO_2.xH_2O$) was used in the amount of 0.09 g as ruthenium oxide. The internal pressure of the autoclave varied to 360–345 kg/cm$^2$G during the reaction. The liquid reaction mixture consisted of two phases and contained, as the total amounts in both of the phases, 25.6 mg of acetic acid, 17.3 mg of methyl acetate, 34.7 mg of ethyl acetate, 5.0 mg of methanol and 27.5 mg of ethanol. The concentration of methane in the unreacted gases in the autoclave was not higher than 0.1 mole %.

EXAMPLE 19

Following the procedure of Example 1, a reaction was carried out except for the employment of 0.4 g of cobalt naphthenate (the cobalt content: 10%) in lieu of 0.12 g of dicobalt octacarbonyl.

In the course of the reaction, the internal pressure of the autoclave changed to 365–350 kg/cm$^2$G.

The liquid reaction mixture(consisting of two phases) contained 86.1 mg of acetic acid, 2.1 mg of methyl acetate, 11.2 mg of ethyl acetate, 1.2 mg of methanol, 4.8 mg of ethanol and a small amount of n-propanol. The concentration of methane in the unreacted gases in the autoclave was not higher than 0.1 mole %.

COMPARATIVE EXAMPLE 1

A reaction was carried out in exactly the same manner as in Example 1, except that n-heptyltriphenyl phosphonium bromide and triphenyl phosphine were both excluded. The reaction pressure reached 340 kg/cm$^2$G at 220° C.

After the reaction, the resulting liquid reaction mixture contained 8.3 mg of methanol, 2.5 mg of ethanol and 1.4 mg of propanol. Neither methyl acetate nor ethyl acetate was detected.

COMPARATIVE EXAMPLE 2

The procedure of Comparative Example 1 was repeated except that dicobalt octacarbonyl was further excluded and the solvent was replaced by 19 ml of sulforan.

The reaction pressure reached 394 kg/cm$^2$G.

The liquid reaction mixture after completion of the reaction contained 33.8 mg of methanol. None of acetic acid, methyl acetate and ethyl acetate was detected.

COMPARATIVE EXAMPLE 3

A reaction was carried out in exactly the same manner as in Comparative Example 1, except that triruthenium dodecacarbonyl was further deleted.

The reaction pressure reached 380 kg/cm$^2$G.

After completion of the reaction, the liquid reaction mixture contained a trace amount of methanol. None of acetic acid, methyl acetate and ethyl acetate was detected.

EXAMPLE 20

Into a stainless steel made autoclave (applied with a liner made of Pyrex glass) having the internal capacity of 50 ml, were charged 0.06 g of ruthenium carbonyl [$Ru_3(CO)_{12}$] (0.28 milligram atom as Ru), 0.032 g of cobalt carbonyl $Co_2(CO)_8$ (0.187 milligram atom as Co), 3.1 g (7 millimoles) of n-heptyltriphenyl phosphonium bromide, 2.01 g (3.5 millimoles) of bis(triphenylphosphine) iminium chloride, 0.087 g (0.28 millimole) of triphenyl phosphite and 15 ml of toluene. Thereafter, synthesis gas (the molar ratio of CO to $H_2=1:1$) was charged at room temperature to 330 kg/cm$^2$G. The autoclave was heated with stirring until its internal temperature reached 240° C., where the autoclave was maintained. While keeping the temperature, synthesis gas was introduced using its pressure regulating valve so as to keep the pressure within the autoclave at 450 kg/cm$^2$G. The reaction was allowed to undergo for 2 hours. Thereafter, the heating of the autoclave and introduction of synthesis gas were stopped. The autoclave was cooled to room temperature and the reaction gas and liquid reaction mixture were taken out of the autoclave and analyzed by gas chromatography. The liquid reaction mixture contained solid matter. Thus, N-methylpyrrolidone was added to the liquid reaction mixture so as to dissolve the solid matter and to form a uniform solution, which was then subjected to an analysis. The liquid reaction mixture contained 12.8 millimoles of acetic acid, 0.5 millimoles of methyl acetate, 2.0 millimoles of ethyl acetate, 0.07 millimoles of methanol, 0.23 millimoles of ethanol, 0.11 millimoles of n-propanol and 1.9 millimoles of propionic acid. In the gas phase, 2.7 millimoles of methane and a trace amount of carbon dioxide gas were detected.

EXAMPLES 21–29

In the same autoclave as that used in Example 20, were charged 0.15 g of ruthenium carbonnyl (triruthenium dodecacarbonyl)—0.7 milligram atom as Ru—, 0.06 g of cobalt carbonyl (dicobalt octacarbonyl)—0.23 milligram moles as Co—, 1.55 g of n-heptyltriphenyl phosphonium bromide, 2.01 g of bis(triphenylphosphine)iminium chloride, 0.23 millimole of a phosphorus compound shown in Table 2 and 15 ml of toluene. Thereafter, synthesis gas (the molar ratio of CO to $H_2=1:1$) was charged at room temperature to 290 kg/cm$^2$G. The autoclave was heated with stirring. When its internal temperature had reached, it was maintained at the same temperature and the above reactants were caused to undergo a reaction. Other reaction conditions and results are summarized in Table 2. In each of the examples, the concentration of methane in the unreacted gases present in the autoclave after completion of the reaction was not greater than 1 mole %, which was not more than 7% of the consumption of carbon monoxide.

TABLE 2

| Ex. No. | Phosphorus compound | Max. reaction pressure (kg/cm² G) | Reaction time (hrs.) | Reaction products (mmoles)[1] | | |
|---|---|---|---|---|---|---|
| | | | | CH₃OH | C₂H₅OH | CH₃COOH |
| 21 | PCl₃ | 365 | 1.1 | 5.17 (6.17) | 5.69 (7.39) | 6.49 (8.43) |
| 22 | 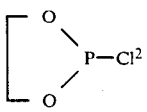 Ethylene chlorophosphite[2] | 390 | 1.1 | 7.75 (10.06) | 5.23 (6.79) | 5.42 (7.04) |
| 23 | P(OH)₃ | 370 | 1.2 | 9.07 (10.80) | 5.71 (6.80) | 4.81 (5.73) |
| 24 | (PhO)₂P(OH) | 360 | 1.0 | 7.48 (10.69) | 4.48 (6.40) | 4.73 (6.76) |
| 25 | (PhO)₃P | 360 | 1.0 | 8.13 (11.61) | 5.02 (7.17) | 5.28 (7.54) |
| 26 | (EtO)₃P | 380 | 1.2 | 6.99 (8.32) | 6.16 (7.33) | 5.50 (6.55) |
| 27 | (Me₂N)₃P | 370 | 1.2 | 10.78 (12.77) | 5.09 (6.06) | 3.81 (4.54) |
| 28 | (Ph)₂P(OBu) | 380 | 1.2 | 13.12 (15.62) | 2.57 (3.06) | 5.55 (6.61) |
| 29 | (Ph)P(OH)₂ | 360 | 0.8 | 10.05 (17.95) | 5.36 (9.57) | 4.46 (7.96) |

Remarks:
[1]Turnover numbers [mole number of product/gram atom number of Ru/reaction time] are shown in brackets ( ).
[2]Ethylene chlorophosphite.

EXAMPLES 30-37

Reactions were respectively carried out similar to Examples 21-29, using ruthenium carbonyl, cobalt calbonyl, promoter and phosphorus compound in their corresponding amounts given in Table 3 and 15 ml of toluene. Results are shown in Table 3. In each of the examples, the concentration of methane present in the unreacted gases in the autoclave was not greater than 1 mole %.

TABLE 3

| Ex. No. | Catalyst (mg-atom) Ru | Catalyst (mg-atom) Co | Promoter (1) | (molar ratio/Ru) | Promoter (2) (P-compound) | (P/Ru atomic ratio) | Maximum reaction pressure (kg/cm² G) | Reaction time (hrs.) | Products (mmole)[1] CH₃OH | C₂H₅OH | CH₃COOH |
|---|---|---|---|---|---|---|---|---|---|---|---|
| 30 | 0.7 | 0.23 | PPNCl HTBr | 5 5 | (PhO)₃P | 1 | 350 | 0.7 | 2.68 (5.47) | 5.25 (10.71) | 5.12 (10.45) |
| 31 | 0.7 | 0.47 | PPNCl HTBr | 5 5 | (PhO)₃P | 1 | 362 | 1.3 | 2.32 (2.55) | 3.66 (4.02) | 7.42 (8.15) |
| 32 | 0.7 | 0.23 | HTBr | 20 | (PhO)₃P | ½ | 380 | 3.0 | 0.24 (0.11) | 1.45 (0.69) | 11.38 (5.42) |
| 33 | 0.7 | 0.23 | HTBr | 20 | (Ph)P(OH)₂ | 1 | 365 | 1.3 | 1.97 (2.16) | 2.54 (2.79) | 9.30 (10.22) |
| 34 | 0.7 | 0.23 | HTBr Pyridine | 20 5 | (Ph)P(OH)₂ | 2 | 340 | 1.0 | 2.78 (3.97) | 2.08 (2.97) | 5.66 (8.09) |
| 35 | 0.7 | 0.23 | TBBr | 20 | (Ph)P(OH)₂ | 1 | 380 | 2.0 | 7.26 (5.19) | 5.15 (3.68) | 4.29 (3.06) |
| 36 | 0.7 | 0.23 | BBCl | 20 | (Ph)P(OH)₂ | 1 | 360 | 1.0 | 9.09 (12.99) | 1.93 (2.76) | 1.73 (2.47) |
| 37 | 0.7 | 0.23 | HTBr | 20 | (PhS)₃P | 1 | 370 | 1.5 | 1.81 (1.72) | 2.21 (2.10) | 8.98 (8.55) |

Remarks:
[1]Turnover numbers [mole number of product/gram atom number of Ru/reaction time] are shown in brackets ( ).

38

Into the same autoclave as that used in Example 20, were charged ruthenium carbonyl (0.28 milligram atom as Ru), cobalt carbonyl (0.093 milligram atom as Co), LiBr as a promoter (32.2 millimoles), triphenyl phosphite as a phosphorus compound (0.28 millimole) and N-ethylpyrrolidine-2-one as a solvent (15 ml). Then, synthesis gas (the molar ratio of CO to H₂=1:1.5) was charged at room temperature to 315 kg/cm²G. The autoclave was heated with stirring to internal temperatures of 245°-250° C. and maintained at those temperatures, thereby causing the reactants to undergo a reaction. The liquid reaction mixture contained, including those present in their ester forms, 1.64 millimoles of methanol, 1.08 millimoles of ethanol and 3.4 millimoles of acetic acid.

In Tables 2 and 3, the amounts of the reaction products are shown as their total amounts by converting those occurred as esters into their corresponding alcohols and acetic acid and then adding the thus-calculated alcohols and acetic acid to methanol, ethanol and acetic acid respectively. In the column containing phosphorus compounds, Ph: phenyl group; PhO: phenoxy group; EtO: ethoxy; BuO: n-butoxy; PhS: phenylthio group; and Me₂N: dimethylamino group. In addition, in the column containing promoters (1), PPNCl: bis (triphenylphosphine)iminium chloride; HTBr: n-heptyltriphenyl phosphonium bromide; TBBr: tetra-n-butyl phosphonium bromide; and BBCl: benzyltri-n-butyl phosphonium chloride.

EXAMPLE 39

Into a stainless steel made autoclave having the internal capacity of 50 ml, were charged 0.15 g of triruthenium dodecacarbonyl, 0.04 g of dicobalt octacarbonyl, 3.10 g of n-heptyltriphenyl phosphonium bromide, 2.01 g of bis(triphenylphosphine)iminium chloride and 15 ml of toluene. Then, a gas mixture of carbon monoxide gas and hydrogen gas (the molar ratio of CO to $H_2 = 1:1$) was charged at room temperature to 300 kg/cm²G. The autoclave was thereafter heated with stirring and maintained at a constant temperature when its internal temperature had reached 240° C. Then, a fresh supply of a gas mixture of carbon monoxide gas and hydrogen gas was additionally charged into the autoclave to raise its internal pressure to 450 kg/cm²G. The autoclave was maintained at the above constant temperature for 0.5 hour, thereby causing the reactants to undergo a reaction. After completion of the reaction, the autoclave was cooled to room temperature and its internal pressure was released. Then, its contents were taken out and subjected to a gas chromatographic analysis The resulting liquid reaction mixture consisted of two separate layers and contained, as the total amounts in both layers, the following reaction products:

Methanol: 48.5 mg (1.52 millimoles)
Ethanol: 66.7 mg (1.45 millimoles)
Acetic acid: 249.0 mg (4.15 millimoles)
Methyl acetate: 83.3 mg (1.13 millimoles)
Ethyl acetate: 46.1 mg (0.52 millimole)

From the gas phase, carbon dioxide and a trace amount of methane were detected.

EXAMPLES 40-52

Using a stainless steel made autoclave having the internal capacity of 50 ml, a reaction was carried out employing each combination of catalysts, promoter(s), solvent and reaction conditions tabulated in Table 4.

Results are shown in Table 4, together with the corresponding reaction parameters employed in Example 39 and the results obtained in the same example.

TABLE 4

| Ex. No. | Catalyst (m-gram atom) | | Promoter (1) (mmole) | | Promoter (2) (mmole) | | Solvent (ml) | Reaction temp. (°C.) | Max. reaction pressure (Kg/cm² G) | Reaction time (hrs.) | Reaction products (mmole) | | |
|---|---|---|---|---|---|---|---|---|---|---|---|---|---|
| | | | | | | | | | | | Methanol | Ethanol | Acetic acid |
| 39 | Ru—A | 0.7 | PPNCl | 7.0 | TPP | 0.23 | T 15 | 240 | 450 | 0.5 | 2.64 | 1.97 | 5.80 |
| | Co—A | 0.23 | HTBr | 7.0 | | | | | | | | | |
| 40 | Ru—A | 0.7 | PPNCl | 3.5 | TPP | 0.23 | T 15 | 220 | 370 | 1.83 | 10.65 | 3.95 | 7.69 |
| | Co—A | 0.23 | HTBr | 3.5 | | | | | | | | | |
| 41 | Ru—A | 0.7 | PPNCl | 3.5 | TPAS | 0.23 | T 15 | 220 | 360 | 1.67 | 9.25 | 3.62 | 5.10 |
| | Co—A | 0.23 | HTBr | 3.5 | | | | | | | | | |
| 42 | Ru—A | 0.7 | PPNCl | 7.0 | TPP | 0.23 | T 15 | 220 | 370 | 0.83 | 14.66 | 3.40 | 3.41 |
| | Co—A | 0.23 | | | | | | | | | | | |
| 43 | Ru—A | 0.7 | PPNCl | 3.5 | TPP | 0.23 | T 15 | 220 | 360 | 1.6 | 11.21 | 2.62 | 2.37 |
| | Co—A | 0.23 | PPNBr | 3.5 | | | | | | | | | |
| 44 | Ru—A | 0.7 | PPNBr | 3.5 | TPP | 0.23 | T 15 | 220 | 380 | 2.25 | 8.01 | 2.60 | 5.14 |
| | Co—A | 0.23 | HTBr | 3.5 | | | | | | | | | |
| 45 | Ru—A | 0.7 | PPNCl | 3.5 | TPP | 0.23 | T 15 | 220 | 365 | 1.25 | 13.87 | 2.72 | 2.65 |
| | Co—A | 0.23 | HTCl | 3.5 | | | | | | | | | |
| 46 | Ru—A | 0.7 | PPNCl | 3.5 | TPP | 0.23 | T 15 | 220 | 365 | 2.08 | 15.29 | 3.65 | 4.99 |
| | Co—A | 0.23 | BBBr | 3.5 | | | | | | | | | |
| 47 | Ru—A | 0.7 | PPNCl | 3.5 | TTP | 0.23 | T 15 | 220 | 362 | 1.33 | 11.50 | 2.70 | 2.65 |
| | Co—A | 0.23 | BBCl | 3.5 | | | | | | | | | |
| 48 | Ru—A | 0.7 | PPNCl | 3.5 | TPP | 0.23 | T 15 | 220 | 365 | 2.08 | 16.17 | 3.95 | 3.97 |
| | Co—A | 0.23 | BuBr | 3.5 | | | | | | | | | |
| 49 | Ru—A | 0.7 | PPNCl | 7.0 | TPP | 0.23 | T 15 | 220 | 355 | 0.75 | 12.07 | 2.74 | 1.80 |
| | Co—A | 0.23 | BBCl | 7.0 | | | | | | | | | |
| 50 | Ru—A | 0.7 | PPNCl | 3.5 | TPP | 0.23 | THF 15 | 220 | 370 | 1.25 | 7.37 | 2.67 | 4.54 |
| | Co—A | 0.23 | HTBr | 3.5 | | | | | | | | | |
| 51 | Ru—A | 0.7 | PPNCl | 3.5 | TPP | 0.23 | A 15 | 220 | 370 | 1.6 | 11.58 | 3.63 | 2.23 |
| | Co—A | 0.23 | HTBr | 3.5 | | | | | | | | | |
| 52 | Ru—A | 0.7 | PPNCl | 3.5 | TPP | 0.23 | ODB 15 | 220 | 370 | 3.0 | 3.53 | 1.56 | 4.37 |
| | Co—A | 0.23 | HTBr | 3.5 | | | | | | | | | |

In each of Examples 40-52, the concentration of methane in the unreacted gases in the autoclave was not higher than 0.1 mole %.

In Table 4, the symbols respectively indicate the following compounds:

Ru-A: Triruthenium dodecacarbonyl [$Ru_3(CO)_{12}$]
Co-A: Dicobalt octacarbonyl [$Co_2(CO)_8$]
T: Toluene
THF: Tetrahydrofuran
A: Anisole
ODB: o-Dichlorobenzene
PPNCl: Bis(triphenylphosphine)iminium chloride
HTBr: n-Heptyltriphenyl phosphonium bromide
TPP: Triphenylphosphine
TPAS: Triphenylarsine
PPNBr: Bis(triphenylphosphine)iminium bromide
HTCl: n-Heptyltriphenyl phosphonium chloride
BBBr: Benzyltributyl phosphonium bromide
BBCl: Bebzyltributyl phosphonium chloride
BuBr: Tetra-n-butyl phosphonium bromide Also in Table 4, each acetate was converted into its corresponding methanol or ethanol and acetic acid and added to the recation products, methanol, ethanol and acetic acid.

What is claimed is:

1. In a process for preparing acetic acid from carbon monoxide gas and hydrogen gas, the improvement which comprises catalytically reacting carbon monoxide gas and hydrogen gas under an elevated pressure and in an aprotic liquid medium selected from the group consisting of a saturated hydrocarbon, an aromatic hydrocarbon, a halogenated hydrocarbon, an ether, an ester, a ketone, an amide, a sulfone and a sulfoxide containing a ruthenium compound, cobalt compound, a basic compound selected from the group consisting of an amine, a phosphine, an arsine, a stibine and a bismuthine and a halide which is at least one member selected from the group consisting of an alkali metal halide, an alkaline earth metal halide, quarternary ammonium halide, a phosphonium halide and an iminium halide.

2. The process as claimed in claim 1 wherein the elevated pressures are 80 to 300 kg/cm²G.

3. The process as claimed in claim 1 wherein the reaction is carried out at 150° to 300° C.

4. The process as claimed in claim 1 wherein the total concentration of the ruthenium compounds and cobalt compound in the liquid medium is within the range of 0.1 to 100 parts by weight as the total weight of pure ruthenium and cobalt based on 1000 parts by weight of the liquid medium.

5. The process as claimed in claim 1 wherein the ruthenium compound and cobalt compound are used at an atomic ratio of 300:1 to 1:10.

6. The process as claimed in claim 1 wherein the basic compound is used in a molar number 0.001 to 10 times the total gram atom number of pure ruthenium and cobalt in the ruthenium and cobalt compounds.

7. The process as claimed in claim 1 wherein the halide is used in a molar number 0.001 to 100 times the total gram atom number of pure ruthenium and cobalt in the ruthenium and cobalt compounds.

8. The process as claimed in claim 1 wherein the halide is a combination of an iminium compound and a phosphonium compound which are respectively represented by the following formula (IV) and (V):

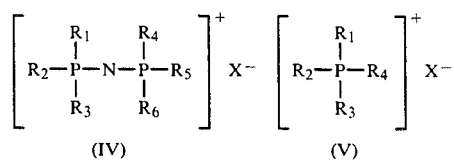

wherein $R_1$, $R_2$, $R_3$, $R_4$, $R_5$ and $R_6$ are individually an alkyl, aryl, alkanol or cycloalkyl group having 1 to 20 carbon atoms, and $X^-$ is an anionic ion.

9. The process as claimed in claim 2 wherein the halide is a combination of an iminium compound and a phosphonium compound which are respectively represented by the following formulae (IV) and (V):

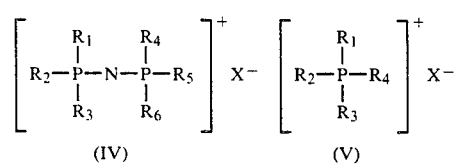

wherein $R_1$, $R_2$, $R_3$, $R_4$, $R_5$ and $R_6$ are individually an alkyl, aryl, alkanol or cycloalkyl group having 1 to 20 carbon atoms and $X^-$ is an anionic ion.

* * * * *

UNITED STATES PATENT OFFICE
CERTIFICATE OF CORRECTION

Patent No. 4,569,948          Dated  February 11, 1986

Inventor(s) Hiroshi Ono, Masao Hashimoto, Eiiti Sugiyama, Kenji Fujiwara, and Kenji Yishida It is certified that error appears in the above-identified patent and that said Letters Patent are hereby corrected as shown below:

Claim 2, line 2, cancel "300 kg/cm$^2$G" and insert --3000 kg/cm$^2$G--.

Signed and Sealed this

Twenty-second Day of July 1986

[SEAL]

Attest:

DONALD J. QUIGG

Attesting Officer          Commissioner of Patents and Trademarks